US00PP37473P2

(12) United States Plant Patent
Li

(10) Patent No.: US PP37,473 P2
(45) Date of Patent: Jun. 16, 2026

(54) ***VERBENA* PLANT NAMED 'KLEVP24182'**

(50) Latin Name: ***Verbena* x *hybrida***
Varietal Denomination: KLEVP24182

(71) Applicant: KLEMM + SOHN GMBH & CO. KG., Stuttgart (DE)

(72) Inventor: Ruijun Li, North Parramatta (AU)

(73) Assignee: Klemm + Sohn GMBH & Co. KG, Stuttgart (DE)

( * ) Notice: Subject to any disclaimer, the term of this patent is extended or adjusted under 35 U.S.C. 154(b) by 0 days.

(21) Appl. No.: 19/264,578

(22) Filed: Jul. 9, 2025

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
See application file for complete search history.

(56) References Cited

U.S. PATENT DOCUMENTS

PP36,256 P2 * 11/2024 Li ..... Plt./308

OTHER PUBLICATIONS https://josvainiugeles.lt/wp-content/uploads/2024/09/Selecta-Annuals-2025.pdf (retrieved online Sep. 15, 2025) (Year: 2024).*

* cited by examiner

*Primary Examiner* — Susan Mccormick Ewoldt
*Assistant Examiner* — Zachariah Allan Kay
(74) *Attorney, Agent, or Firm* — Weatherly IP Solutions, LLC; Karen P. Bechtold; James M. Weatherly

(57) ABSTRACT

A new *Verbena* plant particularly distinguished by a flower color that is bicolored with a purple star surrounded by a white background and an upright and compact round growth habit is disclosed.

1 Drawing Sheet

Genus and species: *Verbena* x *hybrida*.
Variety denomination: 'KLEVP24182'.

BACKGROUND OF THE NEW PLANT

The present invention comprises a new and distinct variety of *Verbena*, botanically known as *Verbena* x *hybrida*, and hereinafter referred to by the variety name 'KLEVP24182'. 'KLEVP24182' originated from a naturally occurring branch mutation of *Verbena* x *hybrida* cultivar 'KLEVP20038' (unpatented) discovered in October 2021 in a nursery in Westland, Netherlands. No stimulus or product was applied to the parent plant to induce the natural mutation resulting in the claimed plant.

In October 2021, 'KLEVP24182' was first vegetatively propagated by vegetative cuttings in Stuttgart, Germany. 'KLEVP24182' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Bicolor flower color comprised of a purple flower surrounded by a white background, and
2. Upright with compact round growth habit

DESCRIPTION OF THE PHOTOGRAPH

This new *Verbena* plant is illustrated by the accompanying photograph which shows the plant's overall plant habit including form, foliage, and flowers. The photograph is of a plant approximately 11-weeks-old grown indoors in Stuttgart, Germany in May 2024. The colors shown are as true as can be reasonably obtained by conventional photographic procedures.

DESCRIPTION OF THE NEW VARIETY

The following detailed descriptions set forth the distinctive characteristics of 'KLEVP24182'. The data which define these characteristics were collected from asexual reproductions carried out in Latina, Italy. Data was collected on three-month-old plants grown in 2023. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* x *hybrida*.
- *Common*.—*Verbena*.
- *Designation*.—'KLEVP24182'.

Parentage: Mutation parent: *Verbena* x *hybrida* cultivar 'KLEVP20038' (unpatented).

Plant:
- *Growth and branching habit*.—Upright with compact round shape.
- *Height* (*from top of soil*).—22.0 cm.
- *Width* (*horizontal plant diameter*).—30.0 cm.
- *Time to produce a finished flowering plant*.—Approximately 8 weeks.
- *Time to initiate and develop roots*.—Two weeks.
- *Root description*.—RHS 155B (White), fine fibrous roots.

Stems:
*Number of branches per plant.*—More than 24.
*Length.*—18.0 cm.
*Diameter.*—0.23 cm.
*Internode length.*—*Approximately* 1.8 cm.
*Color.*—RHS 139D.
*Anthocyanin.*—Absent.
*Texture and appearance.*—Pubescent, round.
Leaves:
*Arrangement.*—Opposite.
*Immature and mature leaf.*—Color: Upper surface: RHS 141A. Lower surface: RHS 141C.
*Length.*—4.3 cm.
*Width.*—1.6 cm.
*Shape.*—Lanceolate.
*Apex.*—Acute.
*Base.*—Obtuse.
*Margin.*—Crenate.
*Texture.*—Upper surface: Leathery. Lower surface: Rugose.
*Venation type.*—Pinnate.
*Venation color.*—Upper surface: RHS 141D. Lower surface: RHS 141D.
*Petioles.*—Length: 0.2 cm. Diameter: 0.1 cm. Color: RHS 141D. Texture: Leathery.
Flower buds:
*Shape.*—Tall, cylindrical.
*Length.*—1.5 cm.
*Diameter.*—0.3 cm.
*Color* (*at tight bud*).—RHS 77B.
Inflorescence:
*Blooming habit* (*flowering season*).—Continuously.
*Lastingness of individual blooms on the plant.*—One week.
*Fragrance.*—Absent.
*Inflorescence type.*—Umbel.
*Length of inflorescence.*—4.6 cm.
*Diameter of inflorescence.*—5.0 cm.
*Number of florets per inflorescence.*—18.
*Peduncle.*—Color: RHS 141A. Length: 2.2 cm. Diameter: 0.1 cm.
Florets:
*Length.*—1.8 cm.
*Diameter.*—2.3 cm.
*Texture.*—Smooth.
*Form.*—Single.
*Color.*—Immature: Upper surface: RHS 77A with white RHS 145D background. Lower surface: RHS 77C with white RHS 145D background. Mature: Upper surface: RHS 77B with white RHS 145D background. Lower surface: RHS 77C with white RHS 145D background.
*Corolla tube length.*—1.2 cm.
*Corolla tube color.*—RHS 157B.
*Petals.*—Length of lobe: 1.0 cm. Diameter of lobe: 0.6 cm. Lobe shape: Obtuse. Apex: Emarginate. Base: Fused to form tube. Margin: Entire. Texture: Upper surface: Glossy, satiny. Lower surface: Glossy, satiny.
*Pedicels.*—Not visible.
Sepals:
*Shape.*—Lanceolate but fused.
*Apex.*—Acute.
*Margin.*—Entire.
*Length.*—0.9 cm.
*Diameter.*—0.2 cm.
*Color.*—RHS 141C.
*Texture.*—Upper surface: Hairy, dull. Lower surface: Hairy, dull.
Reproductive organs:
*Stamens.*—Present.
*Quantity.*—4.
*Appearance.*—Shiny.
*Color.*—RHS 139D.
*Filament length.*—0.3 cm.
*Filament diameter.*—0.1 cm.
*Anther.*—Shape: Elliptic. Color: RHS 141D. Length: 0.2 cm. Diameter: 0.1 cm.
*Pollen amount.*—Sparse.
*Pistils.*—Number: 1. Length: 1.1 cm. Diameter: 0.1 cm. Stigma: Color: RHS 141D. Appearance: Ovate. Length: 0.2 cm. Diameter: 0.1 cm. Style: Color: RHS 141D. Length: 0.9 cm. Diameter: 0.1 cm. Appearance: Long.
Fruit and seed set: To date, fruit and seed development have not been observed on plants.
Disease and pest/insect resistance: Plants of KLEVP24182 have been observed to have good tolerance to powdery mildew (*Podosphaera xanthii*).

COMPARISON WITH PARENTAL LINES AND KNOWN VARIETY

'KLEVP24182' is distinguished from its parent as described in Table 1.

TABLE 1

Comparison with Parental Line

| Trait | Variety 'KLEVP24182' | Mutation parent 'KLEVP20038' (unpatented) |
|---|---|---|
| Flower color | Bi color: purple star with white background | Purple |

'KLEVP24182' is most similar to the commercial *Verbena* variety 'KLEVP20048' (unpatented). Differences between the varieties are described in Table 2.

TABLE 2

Comparison with Similar Variety

| Trait | Variety 'KLEVP24182' | Commercial line 'KLEVP20048' (unpatented) |
|---|---|---|
| Flower color | Bicolor: purple star with white background | Single solid color RHS 72B (strong reddish-purple) |
| Flower size | Smaller than 'KLEVP20048' | Larger than 'KLEVP24182' |

I claim:
1. A new and distinct variety of *Verbena* plant designated 'KLEVP24182' as illustrated and described herein.

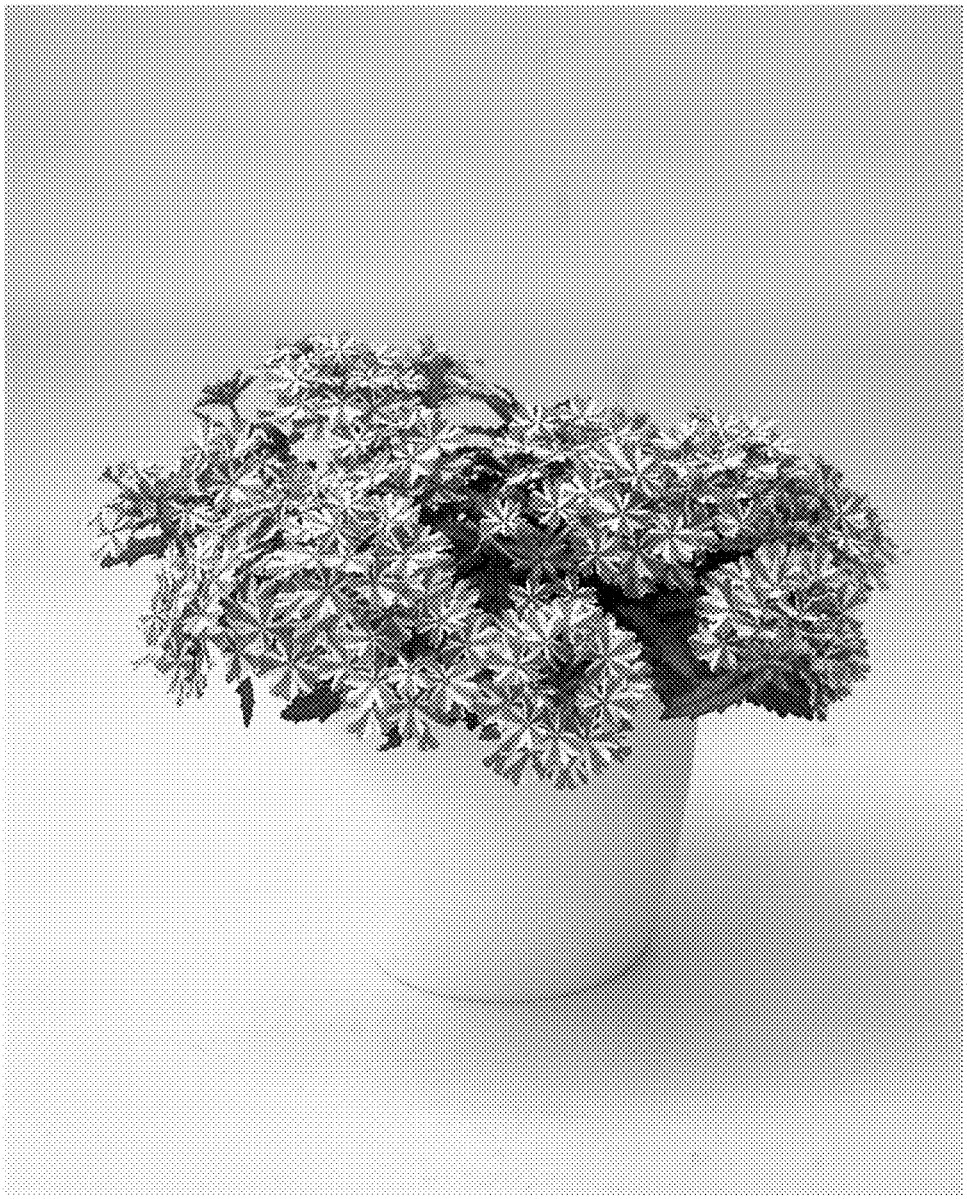

* * * * *